(12) United States Patent  
Kagermeier et al.

(10) Patent No.: US 8,437,009 B2  
(45) Date of Patent: May 7, 2013

(54) SYSTEM AND METHOD FOR THREE DIMENSIONAL RECONSTRUCTION OF AN ANATOMICAL IMPRESSION

(75) Inventors: Robert Kagermeier, Nürnberg (DE); Volker Pritsching, Erlangen (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 286 days.

(21) Appl. No.: 12/820,709

(22) Filed: Jun. 22, 2010

(65) Prior Publication Data

US 2010/0328678 A1    Dec. 30, 2010

(30) Foreign Application Priority Data

Jun. 26, 2009    (EP) .................................... 09163845

(51) Int. Cl.
- *G01B 11/24* (2006.01)
- *G01B 11/00* (2006.01)
- *G01B 11/22* (2006.01)

(52) U.S. Cl.  
USPC ............................ 356/601; 356/625; 356/627

(58) Field of Classification Search ........... 356/600–627  
See application file for complete search history.

(56) References Cited

U.S. PATENT DOCUMENTS

| | | | |
|---|---|---|---|
| 5,428,447 A * | 6/1995 | Toida | 356/601 |
| 2002/0122172 A1 | 9/2002 | Ross, III et al. | |
| 2003/0223083 A1 | 12/2003 | Geng | |
| 2004/0107080 A1 | 6/2004 | Deichmann et al. | |
| 2004/0211903 A1 * | 10/2004 | Bynum et al. | 250/341.1 |
| 2004/0211917 A1 * | 10/2004 | Adamovics | 250/474.1 |
| 2009/0262183 A1 * | 10/2009 | Hayashi et al. | 348/46 |

* cited by examiner

*Primary Examiner* — Michael P Stafira  
(74) *Attorney, Agent, or Firm* — Laurence A. Greenberg; Werner H. Stemer; Ralph E. Locher (57) ABSTRACT

A system and method reconstruct an anatomical impression. The system contains a light signal generating device for generating a light signal directed toward a synthetic test body having the anatomical impression. The light signal is directed toward the synthetic test body such that the light signal is attenuated upon passing through the synthetic test body. A sensor captures the attenuated light signal through the synthetic test body and converts the captured attenuated light signal into digitized image information. The system further includes a digital reconstruction device for reconstructing the digitized image information based on measurement of light attenuation to generate a three-dimensional volume of the anatomical impression.

17 Claims, 6 Drawing Sheets

SYSTEM AND METHOD FOR THREE DIMENSIONAL RECONSTRUCTION OF AN ANATOMICAL IMPRESSION

CROSS-REFERENCE TO RELATED APPLICATION

This application claims the priority, under 35 U.S.C. §119, of European application EP 09163845, filed Jun. 26, 2009; the prior application is herewith incorporated by reference in its entirety.

BACKGROUND OF THE INVENTION

Field of the Invention

The present invention relates to three dimensional reconstruction of anatomical impressions, used for example, for automatically modeling shells for hearing aids.

Hearing aids are used for one or both ears in order to compensate for hearing loss in humans. Hearing aids are typically custom-made because most humans have different levels of hearing loss and different ear canal, meatus and/or concha structures. In order to manufacture a hearing aid or pair thereof, a health care professional takes impressions of a patient's left and right ears on a synthetic material, which are duplicates of the contours of the patient's ears, and then forwards these impressions to a hearing aid manufacturer. The hearing aid manufacturer then replicates the impressions into hearing aid shells so that they fit the patient. Electronic hearing components are then installed into the shells, thus completing the manufacturing process.

The hearing aid shell (or earmold) couples the hearing aid with the subject's ear. Proper fitting of the hearing aid shell to the subject ear canal is required to achieve satisfactory wearing comfort, reduction in acoustic feedback, and unwanted changes in the electro-acoustic characteristics of the aid. Conventionally, the hearing aid shell manufacturing process has been fully manual. As mentioned above, the shell is fabricated as a replica of the impression of the subject's ear (typically the subject's ear canal). However, typical post-impression processes made on the ear impression modify the physical dimensions and the shape of the final shell thus affecting the overall performance of the hearing aid. In recent years, the manufacturing process has been computerized wherein the hearing aid shells are automatically modeled by capturing the 3D contour of the synthetic impression of the subject's ear canal. This is typically done using laser triangulation involving expensive laser scanners or light projection methods and is further limited by the use of two dimensional image processing algorithms.

U.S. patent publication No. 2003/0223083 A1 discloses a three-dimensional imaging method illuminating an object with a light pattern. The light pattern consists of two or more sub-patterns which can encompass the visible light spectrum or can have varying intensity of colored components. A camera detects light reflected from the object.

U.S. patent publication No. 2004/0107080 A1 discloses a method for modeling a customized earpiece, e.g. the housing of a hearing aid. The method includes 3D scanning of an ear impression or the auditory canal. The 3D scanner can detect light reflected from the auditory canal or the impression. It can be a structured light scanner.

U.S. patent publication No. 2002/0122172 A1 discloses a method and system for inspecting lenses based on absorption of light. Absorption of light depends on the thickness of the lenses. Irregularities in the lenses cause variations in light transmission due to variation of absorption and variation of refraction. Based on these principles a 2D scan of the lenses is created. The 2D scan therefore allows to locate irregularities in the lenses.

SUMMARY OF THE INVENTION

It is accordingly an object of the invention to provide a system and a method for three dimensional reconstruction of an anatomical impression which overcome the above-mentioned disadvantages of the prior art methods and devices of this general type.

With the foregoing and other objects in view there is provided, in accordance with the invention a system for reconstructing an anatomical impression. The system contains a light signal generating device for generating a light signal directed toward a synthetic test body defining the anatomical impression, such that the light signal is attenuated upon passing through the synthetic test body resulting in an attenuated light signal. A sensor is provided for capturing the attenuated light signal through the synthetic test body and converts a captured attenuated light signal into digitized image information. A digital reconstruction device for reconstructing the digitized image information based on measurement of light attenuation to generate a three-dimensional volume of the anatomical impression is further provided.

The underlying idea of the present invention is to reconstruct the anatomical impression by capturing an attenuated light signal through a synthetic test body having the impression by a sensor. Accordingly, the present invention uses a synthetic test body made of a synthetic material that is transparent to light, but still attenuates the signal for creating the impression of the inner ear. Digital reconstruction of the impression allows for simple and reliable storage and transmission of the model without handling a physical object. Embodiments of the present invention would advantageously provide a cost effective 3D scanner that can be manufactured in very small sizes, while providing a high accuracy of measurement.

In a preferred embodiment, the proposed system contains a rotatable receiving device for receiving the synthetic test body.

In a further embodiment, the system further contains a measurement control device for controlling an angle rotation of the receiving device, and recording a value for the angle of rotation for each measurement, wherein the digital reconstruction device is further adapted for reconstructing the digitized image information based upon the recorded values for angles of rotation.

In one embodiment, the sensor contains a line sensor. A line sensor provides for faster measurement of light attenuation since it involves comparison of entire lines of pixels, instead of a pixel-by-pixel comparison. Alternately, in another embodiment, the sensor contains a surface sensor. A surface sensor is able to sample a large amount of data for a given time and hence provides high speed and accuracy.

In yet another embodiment, the sensor contains a circular line sensor and the light signal generating device contains a plurality of circularly arranged light signal sources, the plurality of circularly arranged light signal sources and the circular line sensor are arranged on parallel planes and circularly surrounding the test body. The system further contains a device for controlling a linear motion of the test body along a direction perpendicular to the planes and for controlling the temporal order of illumination of the light signal sources. This embodiment requires only a linear motion of the test body, thus obviating the need for any rotational motion.

In a still alternative embodiment, the sensor contains a circular array of surface sensors and the light signal generating device contains a plurality of circularly arranged light signal sources. The plurality of circularly arranged light signal sources and the circular array of surface sensors being arranged on parallel planes and circularly surrounding the test body. The system further contains a device for controlling the temporal order of illumination of the light signal sources. With this embodiment it would be possible to eliminate any movement (rotational or linear) of the test body as well as the sensor/light signal generating device.

In one embodiment, the light signal contains a beam of a laser. A laser beam has a narrow wavelength spectrum (i.e. substantially monochromatic), providing higher accuracy in reconstruction. The laser beam used herein may include visible, ultra-violet or infra-red laser.

In an exemplary embodiment, the sensor contains a CMOS (complimentary metal-oxide semiconductor) image sensor. A CMOS image sensor provides a higher dynamic range than a CCD image sensor, thereby avoiding saturation of pixels. Using local irradiation of the sensor, and in the absence of attenuation through the test body, even weak signals can be captured with adequate resolutions for subsequent reconstruction.

In a preferred embodiment, to minimize distortion in measurement and increase measurement accuracy, the system further contains a grid interposed between the sensor and the test body and adapted to restrict scattering of the light signal through the test body.

In one embodiment, the digital reconstruction device is adapted for reconstructing the digitized image information by a computed tomography (CT) based measurement of light attenuation through the test body. In this manner, a high resolution (in the μm-range) can be achieved. Further advantageously, such a CT based light penetration/attenuation measurement does not pose a problem of undercutting, which is critical in case of laser scanners and projection processors.

According to one aspect of the present invention, the system contains the synthetic test body, the synthetic test body being made of a light attenuating material.

In an exemplary embodiment, the impression is an impression of an ear canal. Herein, the present invention may be used for modeling of a shell for a hearing aid (earmold). Alternately, in another impression, the impression is an impression of a dental contour. Herein, the present invention may be used, for example, for modeling of a tooth crown.

Other features which are considered as characteristic for the invention are set forth in the appended claims.

Although the invention is illustrated and described herein as embodied in a system and a method for three dimensional reconstruction of an anatomical impression, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Embodiments of the present invention are described herein below, particularly referring to modeling of shells for hearing aids. It should be appreciated that the present invention may be used for reconstructing any anatomical impression taken on a synthetic light attenuating material.

Figure 1:
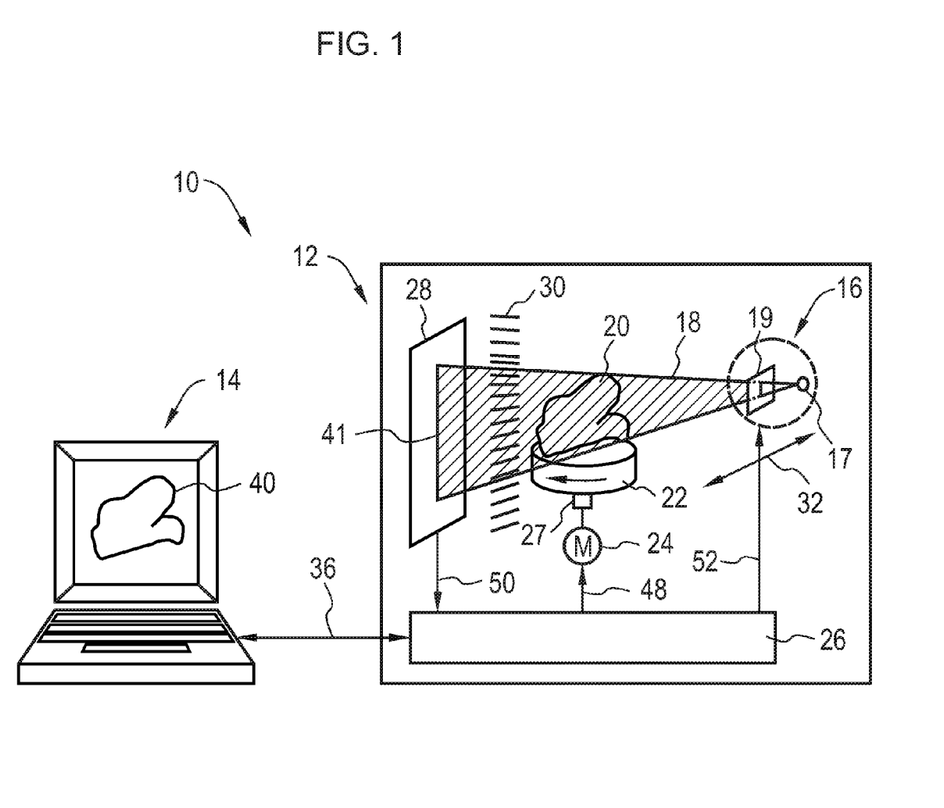
FIG. 1 is a schematic drawing of a system for reconstructing an anatomical impression using a line laser, according to a first embodiment of the invention.

Referring now to the drawings, wherein like characters designate like or corresponding parts, there is shown in FIG. 1 a system 10 for reconstructing an anatomical impression according to one embodiment of the present invention. The anatomical impression, which in this example is an impression of an ear canal of a subject, is taken on a test body 20 made of a synthetic material that is generally transparent to light but attenuates light passing through it. The system 10 broadly includes a scanning unit 12 and digital reconstruction device 14. The scanning unit 12 includes a light signal generating device 16 for generating a light signal 18 directed towards the synthetic test body 20 having the impression of the subject's ear canal. The light signal generating device 16 includes a radiation source 17 and a beam shaping device 19 adapted to provide a desired beam cross-section to the light signal 18. Alternately, the light signal generating device 16 may include, for example, a video projector programmable to generate a light signal having a desired beam cross-section. In the illustrated example, the light signal 18 includes a laser beam, which may include visible, ultra-violet or infra-red laser. Use of a laser is advantageous since laser has a narrow wavelength spectrum, providing higher accuracy in reconstruction. The laser beam used herein may include visible, ultra-violet or infra-red laser. However, in principle, the light signal 18 can include light in any form, although a monochromatic light signal would provide higher measurement accuracy.

The test body 20 is received by a rotatable receiving device 22, which may include, for example, a rotatable mechanical platform. In one embodiment, the receiving device 22 may include a clamping or fastening device for securely supporting the test body 20 as it rotates. The receiving device 22 is rotatably driven by a motor 24. The angle of rotation of the receiving device 22 for each scan is measured by an angle sensor/encoder 27. The angle sensor/encoder may not be required if a high-resolution stepper motor is used in place of the motor 24. The measurements are controlled by measurement control device 26, including, for example, an embedded microcontroller, a field programmable gate array (FPGA) or even a small embedded computer. The measurement control device 26 controls the angle of rotation of the receiving device 22 (i.e., of the test body 20) during the measurement. The value of the angle of rotation of the test body 20 is recorded for every scan, which, along with the measured light attenuation through the test body 20, is fed to the digital reconstruction device for generating the 3D image. In some embodiments described below, the measurement control device 26 may also be adapted to control the positions of the light signal generating device 16 and/or the sensor 28. Communication links 48, 50 and 52 couple the measurement control device 26 respectively to the motor 24, the sensor 28 and the light signal generating device 16.

The light signal 18 is attenuated upon passing through the rotating test body 20, and the attenuated light signal is captured by a sensor 28 arranged opposite to the light signal generating device 16. In other words, the light signal generating device 16 and the sensor 28 are located on opposite sides of the receiving device 22 with the synthetic test body 20. In order to restrict scattering of light, an interspaced grid 30 is placed between the sensor 28 and the test body 20. The grid 30 ensures that only the attenuated light is measured since scattered light causes distortion in the measurement. Using a grid 30 thus increases measurement accuracy by minimizing such distortion. The sensor 28 may include, for example a CCD image sensor, or a CMOS image sensor, which, in turn may be a line sensor, a surface sensor, or even a point sensor. A CMOS image sensor provides a higher dynamic range compared to a CCD image sensor, thereby avoiding saturation of pixels. Using local irradiation of the sensor, and in the absence of attenuation through the test body, even weak signals can be captured with adequate resolutions. The sensor 28 converts the captured attenuated signal into digitized image information. The measurement control device 26 receives the digitized image information from the sensor 28 and transmits the same, along with the stored values of angles of rotation of the test body 18 to the digital reconstruction device 14.

The digital reconstruction device 14 measures the signal attenuation due to the penetration of the light signal through the test body and subsequent irradiation of the sensor 28, and based upon this measurement and the stored angles of rotation of the test body 18 for every scan, reconstructs a three-dimensional volume 40 of the impression. In one embodiment, the signal attenuation due to the penetration/irradiation may be measured based on light-based computed tomography (CT), and from this, the 3D volume 40 may be reconstructed using a CT algorithm. In this manner, a high resolution (in the µm-range) can be achieved. Further advantageously, such a CT based light penetration/attenuation measurement does not pose a problem of undercutting, which is critical in case of laser scanners and projection processors.

The digital reconstruction device 14 may include, for example a commercial PC (such as a desktop or a notebook), coupled to the interfacing device 26 via a USB cable 36 including supply voltage. In an alternate embodiment, depending on the processing capacity required, instead of having a commercial PC, the digital reconstruction may carried out by an embedded microcontroller, FPGA, or a small embedded computer provided, for example, within the measurement control device 26.

In the embodiment shown in FIG. 1, the light signal 18 is shaped by the beam shaping device 19 to form a line laser, i.e. a laser beam is shaped to have a narrow beam cross-section, in the form of a straight line 41. Using a line laser makes it possible to use a line sensor, i.e. a 1-dimensional camera, as the sensor 28. A line sensor provides faster measurement of light attenuation since it involves comparison of entire lines of pixels, instead of a pixel-by-pixel comparison. However, for even higher speed and accuracy, a surface sensor, i.e. a 2-dimensonal camera, may be alternatively used, since a surface sensor is able to sample larger amount of data than a line sensor. In such a case, for every angular position of the test body 20, the measurement control device 16 generating the line laser is imparted a motion along a horizontal scanning direction 32, along the width of the surface sensor 28. Accordingly, the measurement control device 26 is adapted to control the horizontal movement of the measurement control device 16 and to record the angle of rotation of the test body 20 for every horizontal travel of the light signal generating device 16. The recorded values of the angles of rotation of the test body 20 and the measured light attenuation through the test body 20 are subsequently used for the digital reconstruction as described above. Alternately, in case of a surface sensor, it is possible to obviate the motion of the light signal generating device by generating a laser beam that is shaped by the beam shaping device to have a broader cross-sectional area.

Figure 2:
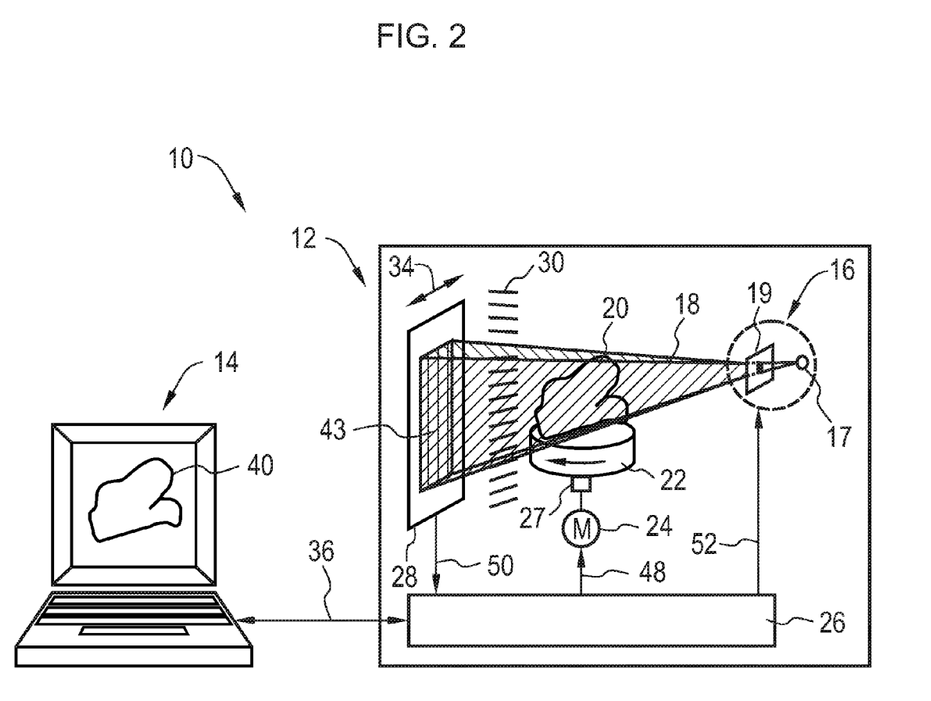
FIG. 2 is a schematic drawing of a system for reconstructing an anatomical impression using a broad laser beam, according to a second embodiment of the invention.

Several other modifications may be considered. For example, as shown in FIG. 2, a line sensor may be used in conjunction with a broad laser beam having a beam cross-section in the form of a rectangle 43. Herein, the line sensor 28 is imparted a motion along a horizontal direction 34 along the width of the laser beam 18, for every angular position of the test body 20. The measurement control device 26 herein is adapted to control the horizontal travel of the line sensor 28 and also record the angle of rotation of the test body 20 for every horizontal scan of the line sensor 28, which is utilized subsequently for the reconstruction of the 3D image as described earlier.

Figure 3:
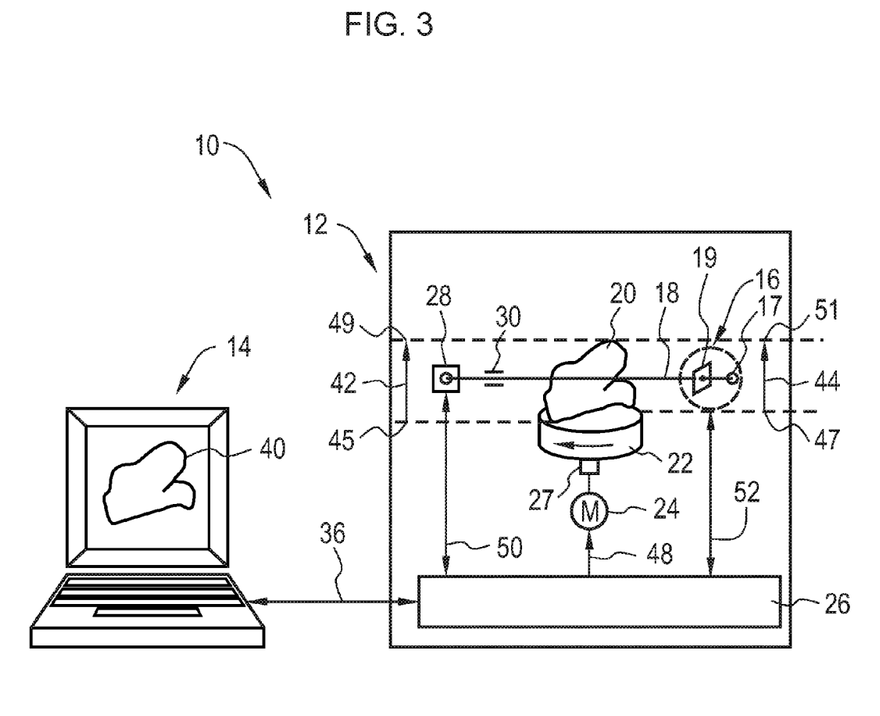
FIG. 3 is a schematic drawing of a system for reconstructing an anatomical impression using a point shaped laser, according to a third embodiment of the invention.

In yet another embodiment shown in FIG. 3, the sensor 28 includes a point sensor, and the light signal 18 is shaped by the beam shaping device 19 to form a point shaped laser beam. Point shaped laser refers to a laser beam having a very low beam cross-sectional area, approaching a point. Herein, for every angular position of the test body 20, the sensor 28 and light signal generating device 16 are synchronously imparted a vertical motion (from bottom to top) along the directions 42 and 44 respectively. The vertical travel of the sensor 28 and the light signal generating device 16 corresponds to the total height of the test body 20 ranging from respective lower extreme positions 45 and 47 to respective upper extreme positions 49 and 51. Herein again, the measurement control device 26 controls the vertical movement of the point sensor 28 and the light signal generating device 16 and records the angle of rotation of the test body 20 for every vertical scan of the point sensor 28 and light signal generating device 16. An advantage of this embodiment is that use of a point sensor substantially reduces measurement of scattered light.

It should be appreciated that although in the illustrated embodiments, a rotatable receiving device 22 is used for imparting rotation of the test body with respect to the sensor 28, relative rotational motion between the test body 20 and sensor 28 may be alternatively achieved by rotation of the sensor 28 and light signal generating device 16 about the test body 20 held stationary. Still alternately, it may be possible to obviate rotational motion of the test body 20 by providing an arrangement shown schematically in FIG. 4. Herein the sensor 28 is a ring-shaped circular line sensor, i.e., a sensor capable of capturing the image of a circular line of extremely small width, for example, of one pixel. The light signal generating device 16 in this embodiment contains an array circularly arranged light signal sources 17. The circular array of light sources 17 and the circular line sensor 28 are arranged on parallel planes and circularly surrounding the test body 20. The light signal 18 from each light source 17 is directed at an angle $\theta$ ($\theta$ having a non-zero value) to the planes formed by the array light sources, such that the light signal 18 with passes through the test body 20 and the attenuated light signal through the test body 20 is captured by the sensor 28.

Figure 4:
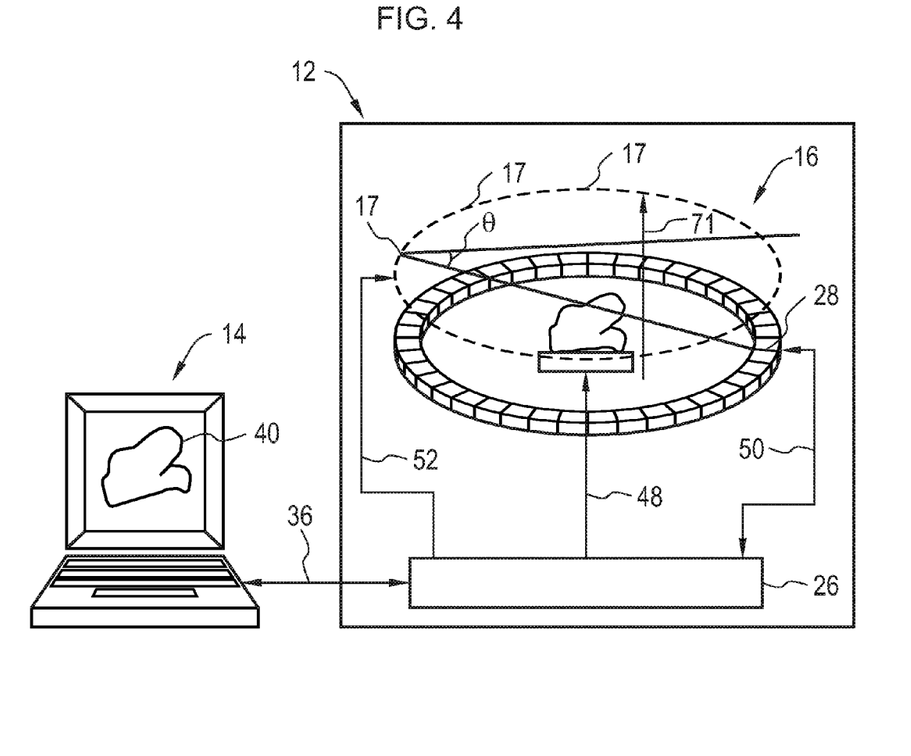
FIG. 4 is a schematic drawing of a system for reconstructing an anatomical impression using a circular line sensor, according to a fourth embodiment of the invention.

Although not explicitly shown, a circular shaped grid may be disposed before the circular line sensor 28 to reduce the scatter of the attenuated light signal through the test body 20. Each light source 17 typically has associated beam shaping devices (not explicitly shown) to shape the light signal 18 to have a line-shaped or a rectangular-shaped beam cross-section. For the purpose of measurement, the light sources 17 are illuminated one by one and the test body 20 is imparted a linear motion along a direction 72 (in this example, in a vertical direction) perpendicular to the planes formed by the light sources 17 and the ring-shaped circular line sensor 28. The linear travel of the test body 20 corresponds to the height of the test body 20. The measurement control device 26 is herein adapted to control the linear motion of the test body 20 and the temporal order of illumination of the light sources 17. For example, in one embodiment, the linear motion imparted to the test body 20 is discrete, wherein, for every discrete position of the test body 20, the test body 20 is scanned by illuminating all the light sources 17 one by one, before the test body 20 is moved linearly to the next discrete position. The measurement control device 26 records the discrete positions of the test body 20 and the recorded values for these positions as well as the measured light attenuation through the test body 20 are subsequently used for reconstructing the 3D volume of the test body 20. In an alternate embodiment, instead of a discrete linear motion, a continuous linear motion may be imparted to the test body 20. However, in such a case, the speed of the linear travel of the test body 20 should be much slower than the rate of temporal illumination of the light sources 17, to provide sufficient data for 3D reconstruction.

Figure 5:
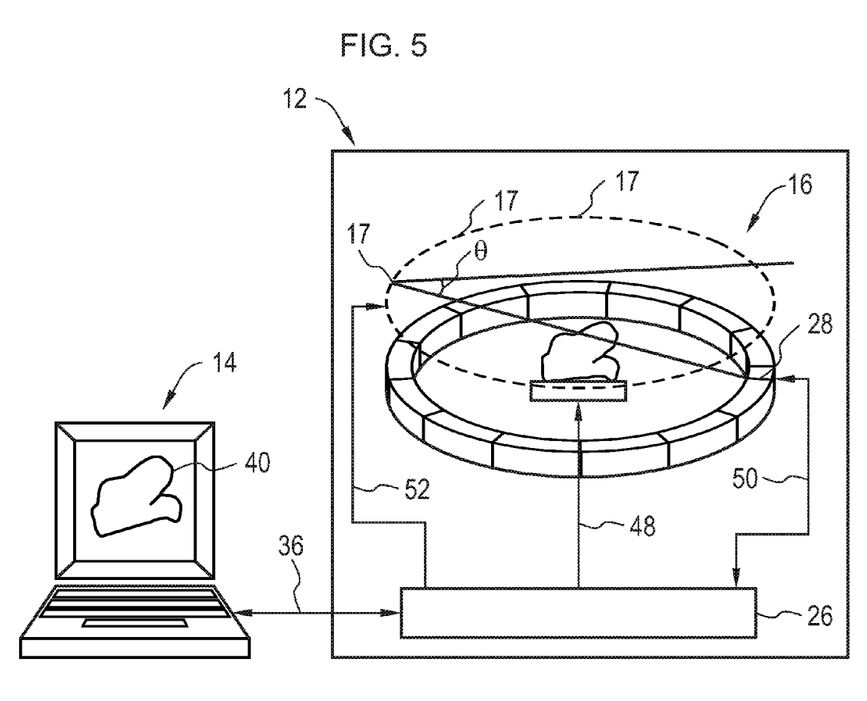
FIG. 5 is a schematic drawing of a system for reconstructing an anatomical impression using circularly arranged array of surface sensors, according to a fifth embodiment of the invention.

In yet another embodiment shown in FIG. 5, the sensor 28 contains a circular array of surface sensors 28 (i.e., 2-dimensional cameras) and the light signal generating device 16 contains a circular array of light signal sources 17. The circular array of light sources 17 and the circular array of surface sensors 28 are arranged on parallel planes and circularly surrounding the test body 20. The light signal 18 from each light source 17 is directed at an angle θ (θ having a non-zero value) to the planes formed by the array light sources, such that the light signal 18 with passes through the test body 20 and the attenuated light signal through the test body 20 is captured by a corresponding surface sensor 28. Again, though not explicitly shown, a circular shaped grid may be disposed before the circular array of surface sensors 28 to reduce the scatter of the attenuated light signal through the test body 20. The light signal 18 in this case is shaped, for example by a beam shaping device (not explicitly shown), to have rectangular-shaped beam cross-section. For the purpose of measurement, the light sources 17 are illuminated one by one. The measurement control device 26 is adapted to control the temporal order of illumination of the light sources 17. The measurement control device 26 further records, for every scan, the light source that is illuminated and/or the corresponding surface sensor and communicates this information to the digital reconstruction device 14 along with the measured light attenuation through the test body 20, for reconstruction of the 3D volume of the test body 20. In this embodiment, the need for linear motion of the test body 28 is eliminated by ensuring that the width of each surface sensor 28 is at least equal to the height of the test body 20.

The above-described embodiments of the present invention provide several advantages. For example, the illustrated embodiments provide a cost effective 3D scanner that can be manufactured in very small sizes. Moreover, the proposed system allows the use of conventional components (laser, CCD/CMOS surface/line sensor) which are commercially available. Furthermore, using a CT based measurement of light attenuation provides highly accurate measurement, in the μm-range. Also, undercutting does not pose a problem for the CT based attenuation measurement, which this is very critical in the case of laser scanners and projection processes. Further advantageously, the digital reconstruction can be done on a commercial PC (desktop/notebook), thus obviating the need for any complex, device specific controls.

Figure 6:
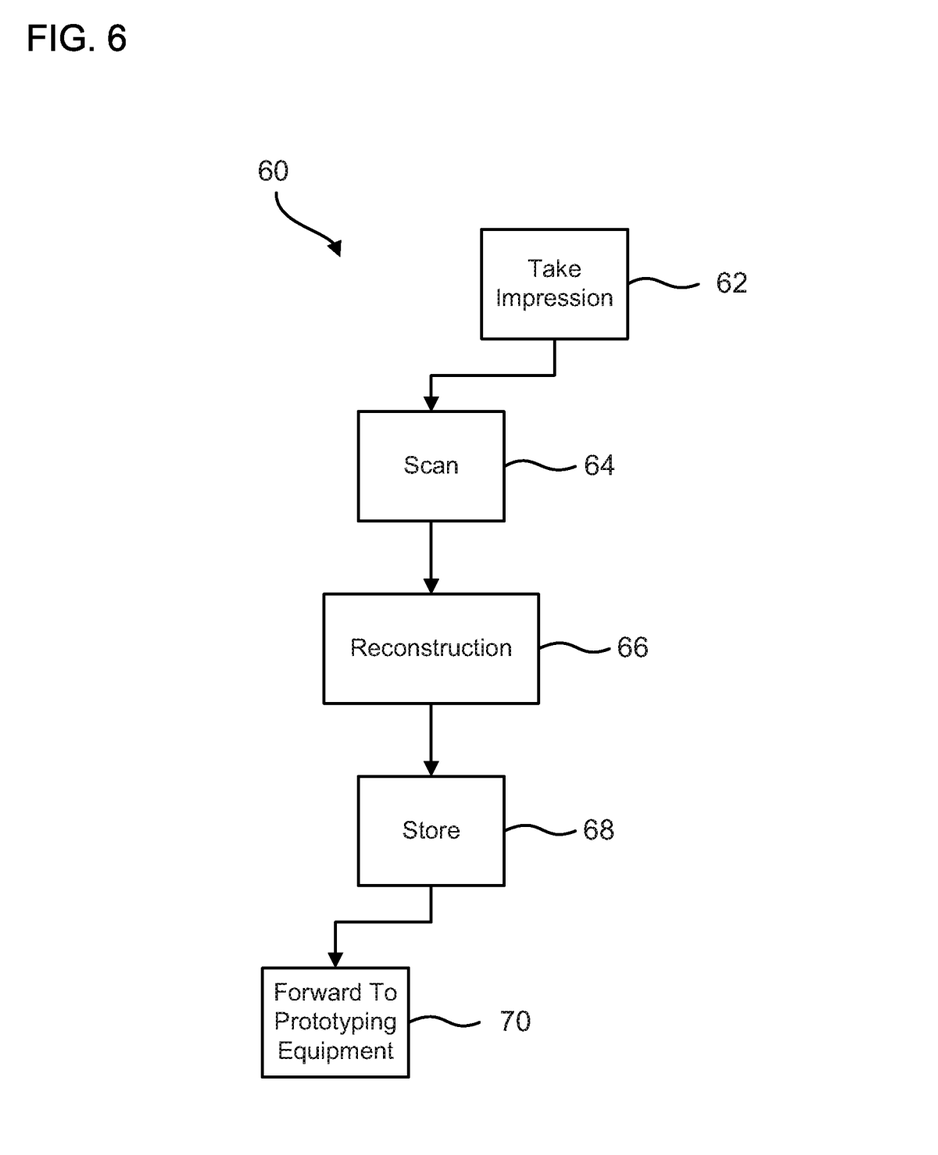
FIG. 6 is a flowchart illustrating an exemplary method for making a hearing aid shell based upon the present invention.

FIG. 6 is a flowchart illustrating an exemplary method 60 for making a hearing aid shell or earmold based upon the teachings of the present invention. At block 62, an impression of the subject's ear canal is taken, for example, by a healthcare professional, on a synthetic test body made of light attenuating material. The test body containing the impression is then forwarded to the hearing aid manufacturer. At block 64, the test body is scanned by directing a light signal towards the test body and imparting rotation to the test body. The attenuated light signal through the test body is captured and converted into digitized image information. Block 66 involves reconstruction of the digitized information to generate a 3D volume of the impression. The reconstruction in block 66 may include a CT based measurement of the light attenuation through the test body and a CT based algorithm to generate the 3D volume of the impression. The reconstructed volume of the impression may then be digitally stored (block 68) and subsequently fed to prototyping equipment (block 70), including, for example dedicated CAD 3D printing machines, to model the earmold and thus achieve the best possible fit. As can be seen, with this approach, post-impression processes are no more needed because the digitally reconstructed impression can be directly fed to rapid prototyping equipments, thus achieving a better accuracy in obtaining an exact replica of the ear impression. Furthermore, digital reconstruction of the impression allows for simple and reliable storage and transmission of the model without handling a physical object. Once the earmold is manufactured, electronic hearing components are subsequently installed into the earmold, thus completing the manufacturing process for the hearing aid.

As mentioned above, invention may be used for reconstructing any anatomical impression taken on a synthetic light attenuating material. Several possible applications of the present invention can be contemplated. As an example, the proposed system and method may be used for reconstruction of an impression dental contour, which may be used for modeling and manufacture of a dental crown, which is a tooth-shaped cover placed over a tooth that is badly damaged or decayed.

Summarizing, the present invention provides a system and method for reconstructing an anatomical impression. The proposed system contains light signal generating device for generating a light signal directed toward a synthetic test body having the anatomical impression. The light signal is directed toward the synthetic test body such that the light signal is attenuated upon passing through the synthetic test body. A sensor captures the attenuated light signal through the test body and converts the captured attenuated light signal into digitized image information. The system further includes digital reconstruction device based on measurement of light attenuation for reconstructing the digitized image information to generate a three-dimensional volume of the anatomical impression.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore contemplated that such modifications can be made without departing from the spirit or scope of the present invention as defined by the below-mentioned patent claims.

The invention claimed is:

1. A system for reconstructing an anatomical impression, the system comprising:
    a light signal generating device for generating a light signal directed toward a synthetic test body defining the anatomical impression, such that the light signal is attenuated upon passing through the synthetic test body resulting in an attenuated light signal;
    a sensor for capturing the attenuated light signal through the synthetic test body and converting a captured attenuated light signal into digitized image information; and
    a digital reconstruction device for reconstructing the digitized image information based on measurement of light attenuation to generate a three-dimensional volume of the anatomical impression.

2. The system according to claim 1, further comprising a rotatable receiving device for receiving the synthetic test body.

3. The system according to claim 2, further comprising a measurement control device for controlling an angle of rotation of the rotatable receiving device, and recording a value for an angle of rotation for each measurement, wherein said digital reconstruction device is further adapted for reconstructing the digitized image information based upon recorded values for angles of rotation.

4. The system according to claim 1, wherein said sensor has a line sensor.

5. The system according to claim 1, wherein said sensor has a surface sensor.

6. The system according to claim 1,
    wherein said sensor contains a circular line sensor;
    wherein said light signal generating device contains a plurality of circularly arranged light signal sources, said plurality of circularly arranged light signal sources and said circular line sensor are disposed on parallel planes and circularly surrounding the synthetic test body; and
    further comprising a device for controlling a linear motion of the test body along a direction perpendicular to planes and for controlling a temporal order of illumination of said light signal sources.

7. The system according to claim 1,
    wherein said sensor has a circular array of surface sensors;
    wherein said light signal generating device has a plurality of circularly disposed light signal sources, said plurality of circularly disposed light signal sources and said circular array of surface sensors are disposed on parallel planes and circularly surrounding the synthetic test body; and
    further comprising a device for controlling a temporal order of illumination of said light signal sources.

8. The system according to claim 1, wherein the light signal contains a beam of a laser.

9. The system according to claim 1, wherein said sensor contains a complimentary metal-oxide semiconductor image sensor.

10. The system according to claim 1, further comprising a grid interposed between said sensor and the synthetic test body and adapted to restrict scattering of the light signal through the synthetic test body.

11. The system according to claim 1, wherein said digital reconstruction device is adapted for reconstructing the digitized image information based on a computed tomography based measurement of light attenuation through the synthetic test body.

12. The system according to claim 1, wherein the synthetic test body is made of a light attenuating material and is part of the system.

13. The system according to claim 1, wherein the anatomical impression is an impression of an ear canal.

14. The system according to claim 1, wherein the anatomical impression is an impression of a dental contour.

15. A method for reconstructing an anatomical impression, which comprises the steps of:
    generating a light signal and directing the light signal toward a synthetic test body, such that the light signal is attenuated upon passing through the synthetic test body;
    capturing the attenuated light signal through the synthetic test body and converting captured attenuated light signal into digitized image information; and
    reconstructing the digitized image information based on measurement of light attenuation to generate a three-dimensional volume of the anatomical impression.

16. The method according to claim 15, which further comprises:
    imparting a rotational motion to the synthetic test body; and
    recording a value for an angle of rotation of the synthetic test body for each measurement, wherein the reconstructing of the digitized image information based upon recorded values for angles of rotation.

17. The method according to claim 15, wherein the reconstructing of the digitized image information includes a computed tomography based measurement of light attenuation through the synthetic test body.

* * * * *